US012594683B2

(12) United States Patent
Boamfa et al.

(10) Patent No.: US 12,594,683 B2
(45) Date of Patent: Apr. 7, 2026

(54) HAIR-CUTTING HEAD AND HAIR-CUTTING DEVICE

(71) Applicant: KONINKLIJKE PHILIPS N.V., Eindhoven (NL)

(72) Inventors: Marius Iosif Boamfa, Veldhoven (NL); Babu Varghese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 28 days.

(21) Appl. No.: 18/711,889

(22) PCT Filed: Nov. 17, 2022

(86) PCT No.: PCT/EP2022/082172
§ 371 (c)(1),
(2) Date: May 21, 2024

(87) PCT Pub. No.: WO2023/094245
PCT Pub. Date: Jun. 1, 2023

(65) Prior Publication Data
US 2025/0010502 A1 Jan. 9, 2025

(30) Foreign Application Priority Data
Nov. 23, 2021 (EP) .................................... 21209849

(51) Int. Cl.
*B26B 19/46* (2006.01)
*A61N 5/06* (2006.01)
(Continued)

(52) U.S. Cl.
CPC ............ *B26B 19/46* (2013.01); *A61N 5/0616* (2013.01); *B26B 19/14* (2013.01); *B26B 19/388* (2013.01);
(Continued)

(58) Field of Classification Search
CPC ....... B26B 19/46; B26B 19/14; B26B 19/388; B26B 19/48; A61N 5/0616; A61N 2005/0663
See application file for complete search history.

(56) References Cited

U.S. PATENT DOCUMENTS 11,964,404 B2 *   4/2024   Wierstra ................. B26B 19/48
2006/0207104 A1 *   9/2006   Alvite .................. A01K 13/002
30/216

(Continued)

FOREIGN PATENT DOCUMENTS

CN   2848495 Y   12/2006
CN   112873286 A   6/2021
(Continued)

OTHER PUBLICATIONS

Papageorgiou et al., "Phototherapy with blue (415 nm) and red (660 nm) light in the treatment of acne vulgaris" British Journal of Dermatology, vol. 142 Issue 5, pp. 973-978, (2000).
(Continued)

*Primary Examiner* — Omar Flores Sanchez

(57) ABSTRACT

A hair-cutting head (10) for a hair-cutting device (100) having two sets (22, 24) of light sources which are configured to emit light predominantly in different respective wavelength bands. A first set (22) emits light in a wavelength band of 400-500 nm. A second set (24) emits light in a wavelength band of 500 nm and above. For improved eye safety, the first set of light sources is arranged so that its light output is projected onto the user's skin (23) during operation only via a central region (56) of a skin-contacting area (54) of the hair-cutting head (10). The second set (24) of light sources is arranged so that its light output is provided on the user's skin during operation only via a peripheral region (58) of the same skin-contacting area. This arrangement aims to make it more likely that the light of the first set (24) of light
(Continued)

sources is fully shielded by the contact of skin to the hair-cutting head during normal operation, protecting the eyes from this light.

11 Claims, 3 Drawing Sheets

(51) Int. Cl.

| | | |
|---|---|---|
| *B26B 19/14* | (2006.01) | |
| *B26B 19/38* | (2006.01) | |
| *B26B 19/48* | (2006.01) | |

(52) U.S. Cl.
CPC ...... *B26B 19/48* (2013.01); *A61N 2005/0663* (2013.01)

(56) References Cited

U.S. PATENT DOCUMENTS

| | | | | |
|---|---|---|---|---|
| 2008/0103560 | A1 | 5/2008 | Powell et al. | |
| 2015/0128776 | A1* | 5/2015 | Zuidervaart | B26B 19/388 30/34.2 |
| 2019/0358835 | A1* | 11/2019 | Rao Ganesh | H05B 47/11 |
| 2020/0031004 | A1* | 1/2020 | Khubani | B26B 19/3873 |
| 2022/0055237 | A1* | 2/2022 | Cordani | B26B 19/46 |
| 2022/0355496 | A1* | 11/2022 | Schneider | B26B 19/3813 |
| 2023/0271340 | A1* | 8/2023 | Wierstra | B26B 19/388 30/34.05 |
| 2023/0347534 | A1* | 11/2023 | Lap | B26B 19/146 |
| 2024/0198546 | A1* | 6/2024 | Zjiroecha | B26B 21/48 |
| 2024/0278443 | A1* | 8/2024 | Bisschop | B26B 19/388 |
| 2025/0010093 | A1* | 1/2025 | Varghese | A61B 5/4836 |
| 2025/0010502 | A1* | 1/2025 | Boamfa | B26B 19/388 |
| 2025/0042050 | A1* | 2/2025 | Petrelli | B26B 19/14 |
| 2025/0065520 | A1* | 2/2025 | Vugts | F21V 29/70 |
| 2025/0108529 | A1* | 4/2025 | Deshpande | B26B 19/20 |

FOREIGN PATENT DOCUMENTS

| | | | |
|---|---|---|---|
| DE | 20201967 | U1 | 5/2002 |
| JP | 2005125075 | A | 5/2005 |
| KR | 20200104548 | A | 9/2020 |
| KR | 20200107548 | A | 9/2020 |
| KR | 20210083142 | A | 7/2021 |
| RU | 53163 | U1 | 5/2006 |
| WO | 2008052151 | A2 | 5/2008 |

OTHER PUBLICATIONS

Lee et al., "Blue and Red Light Combination LED Phototherapy forAcne Vulgaris in Patients with Skin Phototype IV", Lasers in Surgery and Medicine vol. 39, Iss. 2, p. 180-188 (2007).
"Photobiological Safety of Lamps and Lamps Systems"—IEC/EN 62471, 2006.
International Search report and Written Opinion of PCT/EP2022/082172, dated Mar. 16, 2023.

\* cited by examiner

HAIR-CUTTING HEAD AND HAIR-CUTTING DEVICE

CROSS-REFERENCE TO PRIOR APPLICATIONS

This application is the U.S. National Phase application under 35 U.S.C. § 371 of International Application No. PCT/EP2022/082172, filed on Nov. 17, 2022, which claims the benefit of European Patent Application No. 21209849.5, filed on Nov. 23, 2021. These applications are hereby incorporated by reference herein.

FIELD OF THE INVENTION

The present invention relates to a hair-cutting head and a hair-cutting device, in particular of a type having light sources incorporated therein for an optical skin treatment function.

BACKGROUND OF THE INVENTION

The invention is in the field of hair-cutting devices, particularly electric shavers which are designed to perform shaving actions and the like in which hairs are cut at a position close to the skin. In general, an electric shaver comprises a shaving unit or shaver head where one or more hair-cutting units are located, wherein the shaving unit comprises a base member for the purpose of supporting the one or more hair-cutting units. A particularly common design of the shaving unit uses three hair-cutting units in a triangular configuration. An electric shaver comprises a main body besides the shaving unit. The main body is normally shaped so as to be suitable to be taken hold of by a user of the shaver and may accommodate various components of the shaver such as an electric motor.

Each hair-cutting unit of the shaving unit comprises a combination of an internal cutting member and an external cutting member which is arranged to cover the internal cutting member, the external cutting member being provided with a series of hair-entry openings for allowing hairs to reach through the external cutting member and encounter the internal cutting member during a shaving action. In a practical design, the external cutting member is generally cup-shaped and has a substantially circular periphery, wherein the hair-entry openings may be shaped like elongated slits extending substantially radially with respect to a central axis of the external cutting member, in one or more annular areas making up one or more hair-cutting tracks. Such an external cutting member is particularly suitable to be used in an electric shaver of the rotary type, i.e. an electric shaver including at least one hair-cutting unit in which the internal cutting member is arranged so as to rotate during operation.

Proper use of the electric shaver involves putting the shaver to an active state, i.e. a state in which the internal cutting member of the at least one hair-cutting unit is rotated, and moving the shaving unit over a portion of skin to be subjected to a shaving action. The external cutting member has a hair-cutting track surface for contacting a portion of skin at the position of the one or more hair-cutting tracks during a hair-cutting action. At positions where the hair-entry openings are delimited, hair-cutting surfaces are present in the external cutting member. In a common design, the internal cutting member includes blades having hair-cutting edges. During a shaving action, hairs entering the hair-entry openings are sheared between the hair-cutting surfaces and the hair-cutting edges, and get cut off at a position close to the skin as a result thereof.

It is known that light can be used for treatment or therapy effects when administered to skin.

For example, blue light can be efficacious in ameliorating acne. Both *Propionibacterium acnes* and Acne Vulgaris induce secretion of coproporphyrin. The absorption of blue light by the coproporphyrin leads to reactive free radical and singlet oxygen production, and eventually to bacterial destruction, which is effective in treating acne. This effect is illustrated by FIG. 1 which shows a graph of the absorption bands of *Propionibacterium acnes* (although a similar band also pertains to acne vulgaris).

By way of further example, red light has an anti-inflammatory effect and stimulates wound recovery.

Furthermore, red and blue light in combination have synergistic effects. Many clinical trials confirmed the superior effect of the mixed blue and red light for the treatment of acne due to the synergy between the anti-bacterial and anti-inflammatory effect of blue and red light, respectively. In this regard, reference is made in particular to the paper: P. Papageorgiou et al., British Journal of Dermatology. 142, p. 973-978 (2000), and to the paper: S. Y. Lee et al. Lasers in Surgery and Medicine 39, p. 180-188 (2007). Some applications require a certain combination/ratio of blue and red light. They can be used sequentially or simultaneously in the treatment of acne vulgaris. Another relevant consideration is the penetration depth of different wavelengths into the skin. The blue light is absorbed at the surface, while the red light is absorbed to a deeper level.

Red and blue light are just two examples. Other light colors or wavebands can also have useful therapeutic effects. For example, violet light has been shown to have effect in treating acne vulgaris, eczema and psoriasis, and to promote wound healing. Near infra-red light has been shown to be effective for improving microcirculation, reducing cellulite, promoting wound healing, addressing surface bacterial infection, providing pain relief and a variety of other beneficial effects. UV light has been shown to have benefit in addressing eczema and psoriasis. Infra-red light can be useful for example for skin healing and skin warming. These represent just a small non-limiting selection to illustrate the fact that different colors of light can be used to provide different combinations of beneficial effects.

It is known to integrate lighting elements into a shaver device to achieve beneficial optical therapeutic effects simultaneously while shaving. The integration of both red and blue LEDs for acne treatment in the shaving unit of an electric shaver is for example disclosed by WO 2008/052151 A2.

SUMMARY OF THE INVENTION

The invention is defined by the claims.

Although integration of light therapy into shaving devices is known per se, it is so far a poorly explored area of development. In a practical product for everyday use, there are many considerations which must be taken into account. Particularly in the case of a facial grooming device such as a shaver, it has been recognized by the inventors of the present invention that integration of lighting units requires careful consideration of eye safety. This is not a consideration that is immediately obvious when considering the technology in abstract, and in the absence of the real-world practical experimentation which has been performed by the present inventors.

By way of further background, the industry standard IEC 62471 relates to photobiological safety of lamps and lamp systems. This describes the norms for eye safety in relation to lighting devices.

FIG. 2 shows a reproduction of one graph from this standard (page 37) which represents the retina blue light hazard $B(\lambda)$ (line 8) and retina burn hazard $R(\lambda)$ (line 6), as a function of wavelength. From this graphical representation, it can be deduced that light in the wavelength range of 400-500 nm has a significantly elevated blue light retina hazard function $B(\lambda)$, as well as a significantly elevated retina burn hazard function $R(\lambda)$.

It has therefore been recognized by the inventors that, when considering eye safety in relation to light output, there is a differing importance in the protection of the user's eyes depending upon the frequency range of the light concerned. It is more important to protect eyes from light in the wavelength range of 400-500 nm than light of wavelengths exceeding 500 nm.

The inventors have therefore sought to find an efficient means for protecting the user from the more harmful light range.

According to examples in accordance with an aspect of the invention, there is provided a hair-cutting head for a hair-cutting device. The hair-cutting head comprises a head housing accommodating at least one hair-cutting unit and a lighting module. The hair-cutting head further comprises a skin-contacting area via which the hair-cutting head is in contact with a user's skin during use of the hair-cutting head. The skin-contacting area has a central area, and further has a lateral area. The lateral area preferably fully surrounds the central area.

The lighting module comprises a first set of at least one light source. Each light source of the first set of at least one light source is configured to emit first light having wavelengths predominantly in a range from 400-500 nm.

The lighting module further comprises a second set of at least one light source. Each light source of the second set of at least one light source is configured to emit second light having wavelengths predominantly in a range above 500 nm.

Each light source of the first set of light sources is arranged to emit, during use of the hair-cutting head with the skin-contacting area in contact with the user's skin, the first light towards the user's skin only via the central area of the skin-contacting area.

Each light source of the second set is arranged to emit, during use of the hair-cutting head with the skin-contacting area in contact with the user's skin, the second light towards the user's skin only via the lateral area of the skin-contacting area.

The solution proposed by the inventors according to the presently claimed invention is to carefully select the positioning of the first and second sets of light sources according to their predominant light output wavelength, so that the more eye-hazardous light sources are centrally located relative to the hair-cutting head, and the less hazardous light sources are more peripherally located relative to the hair-cutting head. By placing the more eye-hazardous light sources more centrally, this aims to achieve a configuration whereby, in normal use of the hair-cutting device, with the hair-cutting head placed against the skin for cutting hairs, the centrally located light sources are more fully covered by the skin being contacted. The skin therefore acts as the light shield, so that there is less likelihood of the light escaping into the eyes of the user than if the relevant light sources were more peripherally located.

The term "hair-cutting head" means a part of a hair-cutting device which engages with the skin of the user to cut hairs. It is the part which interfaces with the skin. It may be separably or removably coupled with a main body part (or handle portion) of the hair-cutting device, or it may be an integral part of the hair-cutting device (i.e. non separable therefrom).

The aforementioned "hair-cutting unit" is a part of the hair-cutting head which actually cuts hairs during operation of the hair-cutting device, with the head attached.

The aforementioned "skin-contacting area" refers to an exposed outer region of the hair-cutting head which is designed to be applicable to the skin during normal use for cutting hair. The skin contacting area in this context encompasses the hair-cutting units which actually cut the hair. The aforementioned central area and lateral area of the skin-contacting area may therefore encompass part or all of the exposed skin-contacting faces of the hair-cutting units. The light sources may optionally in some embodiments (although it is not at all a necessity) be arranged to emit light via at least a part of at least one of the hair-cutting unit(s).

Each of the first light and second light can be understood as having a respective light frequency or wavelength spectrum (i.e. an emission spectrum). Reference to the first light having wavelengths predominantly in a range from 400-500 nm means that the emission spectrum of the first light is such that a majority of the optical power of the first light is provided by wavelength components in the range of 400-500 nm. Likewise, reference to the second light having wavelengths predominantly in a range above 500 nm means that the emission spectrum of the second light is such that a majority of the optical power of the second light is provided by wavelength components in the range above 500 nm.

Further to the above, and in connection with each wavelength range as described herein with reference to the invention and the embodiments thereof, the term "predominantly" implies that at least 80%, preferably at least 90%, and more preferably at least 95% of the optical power of each of the first light and the second light is provided by wavelength components within the respectively defined wavelength range.

The invention covers hair-cutting devices having an electrically driven hair-cutting function, such as the electric shavers as described here before, as well as other types of hair-cutting devices having, for example, non-driven razor blades arranged stationary in a blade cartridge (so-called blade razors for wet use). In such alternative hair-cutting devices such as blade razors, in a similar way each light source of the first set is arranged to emit the first light only via a central portion of a skin-contacting surface of the head housing, e.g. the blade cartridge, and each light source of the second set is arranged to emit the second light only via a lateral portion of the skin-contacting surface of the head housing.

In some embodiments, the lateral area of the skin-contacting area is bounded by a perimeter of the skin-contacting area. In other words, the lateral area is the peripherally outermost area of the skin-contacting area.

More specifically, the lateral area of the skin-contacting area may be bounded by a perimeter of the hair-cutting head. In other words the lateral area is the peripherally outermost area of the hair-cutting head.

The central area means an area which encompasses at least a central point of the skin-contacting area, for example relative to a perimeter of the skin-contact area, and/or relative to a perimeter of the hair-cutting head.

In some embodiments, the hair-cutting head comprises at least two hair-cutting units.

The head housing may comprise a skin-contacting surface arranged to be in contact with the user's skin during use of the hair-cutting head. The skin-contacting surface may comprise, for each respective hair-cutting unit, an individual opening receiving the respective hair-cutting unit.

In other words, the skin-contacting area of the hair-cutting head in this possible arrangement comprises the skin-contacting faces of the hair-cutting units, and further comprises the skin-contacting surface of the head housing arranged between and/or around the hair-cutting units. Another way of describing this is to say that the skin-contacting area comprises a skin-contacting surface of the head housing which delimits openings within which are received the hair-cutting units.

Pursuant to this arrangement, in some embodiments, the aforementioned central area of the skin-contacting area of the hair-cutting head may comprise a central portion of the skin-contacting surface of the head housing arranged centrally between the hair-cutting units. The lateral area of the skin-contacting area of the hair-cutting head may comprise a lateral portion of the skin-contacting surface of the head housing that fully surrounds the central portion of the skin-contacting surface of the head housing and at least partially surrounds each of the hair-cutting units.

Each light source of the first set of light sources may be arranged to emit, during use of the hair-cutting head, the first light towards the user's skin only via the central portion of the skin-contacting surface of the head housing. Each light source of the second set may be arranged to emit, during use of the hair-cutting head, the second light towards the user's skin only via the lateral portion of the skin-contacting surface of the head housing. Thus, in this particular set of embodiments, there is emission of the first and second light only via (parts of) the skin-contacting surface of the head housing.

In some embodiments, the hair-cutting head is in particular for an electric hair-cutting device comprising three hair-cutting units of a rotary type arranged in a tri-angular configuration forming three pairs of adjacent hair-cutting units. This arrangement is known within shaver devices for example.

Each hair-cutting unit may comprise an external cutting member with an annular hair-cutting area having hair-entry openings, and an internal cutting member which is covered by and rotatable relative to the external cutting member. The (aforementioned) central portion of the skin-contacting surface of the head housing may be arranged centrally between the three hair-cutting units. The (aforementioned) lateral portion of the skin-contacting surface of the head housing may comprise three lateral sub-portions that are each respectively arranged between the hair-cutting units of a respective pair of the three pairs of adjacent hair-cutting units. The second set of light sources may comprise, for each respective one of the three lateral sub-portions of the lateral portion of the skin-contacting surface, at least one light source arranged to emit the second light towards the user's skin only via said respective lateral sub-portion. The structure and geometry of this arrangement will become clearer later in this description, with reference to accompanying drawings.

In accordance with one or more embodiments, the first light may have wavelengths predominantly in a range from 400-480 nm. This wavelength range more precisely covers blue light of a type which is known to have therapeutic effects in relation to acne.

In accordance with one or more embodiments, the second light may have wavelengths predominantly in a range from 600-700 nm. This wavelength range more precisely covers red light of a type which is known to have anti-inflammatory effects.

To further enhance the eye safety profile of the device, according to some embodiments, one or more sensor means can be introduced to detect when the hair-cutting head is actually in contact with the skin, and/or when the hair-cutting head is in motion. Activation of light can be dynamically controlled in dependence upon the sensor outputs.

According to some embodiments, the hair-cutting head may comprise a skin contact sensor configured and arranged to detect, during use of the hair-cutting head, contact between at least a region of the skin-contacting area of the hair-cutting head and the user's skin. A controller may further be provided, and adapted to control the lighting module such that at least each light source of the first set of light sources is prevented from emitting the first light when an output signal generated by the skin contact sensor indicates no contact with the user's skin. Thus, at least the light in the more eye-hazardous range is prevented from being emitted when the skin-contacting area is not in contact with the skin, i.e. when the first set of light sources are not being shielded from the user's eyes by contact with the skin.

The skin contact sensor may in some examples be arranged in the central area of the skin-contacting area of the hair-cutting head. In this way, the sensor output more specifically indicates contact of the region of the skin-contacting area via which the higher eye-hazard first light of the first set of light sources is emitted.

Additionally or alternatively, in at least one set of embodiments, the hair-cutting head comprises a motion sensor configured and arranged to detect, during use of the hair-cutting head, motion of the hair-cutting head relative to the user's skin. A controller may further be provided, which is adapted to control the lighting module such that at least each light source of the first set is prevented from emitting the first light when an output signal generated by the motion sensor indicates, relative to the user's skin, no motion of the hair-cutting head or motion of the hair-cutting head at a speed below a predefined threshold speed. This further enhances safety by avoiding over-exposure of the skin to the light. For example, over exposure may occur if the user holds the hair-cutting head in a stationary position on the skin or when the user moves the hair-cutting head at too low a speed.

Furthermore, the motion sensor also enhances eye safety by further restricting the time periods during operation when the high eye-hazard light sources of the first set are activated. In particular, the activation periods are restricted to only those times when the hair-cutting head is being swept across the skin, i.e. when the device is actively being engaged to cut hair. It is predominantly only during these periods that the therapeutic effects of the light are needed or are advantageous.

In some examples, the light intensity of the light sources could be controlled as a function of the measured speed to obtain a same level of light exposure at different speeds.

Another aspect of the invention is a hair-cutting device comprising a handle portion and a hair-cutting head coupled to the handle portion. The hair-cutting head is a hair-cutting head in accordance with any embodiment or example described in this disclosure, or in accordance with any claim of this patent application.

In some embodiments, the hair-cutting device is an electric shaver. However, as discussed above, this is not essential.

In some embodiments, the handle portion comprises a main housing of the electric shaver accommodating an electric motor. The hair-cutting head may be a shaving unit. The electric motor may be configured and arranged to drive each of the hair-cutting units of the shaving unit when the shaving unit is coupled to the main housing.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
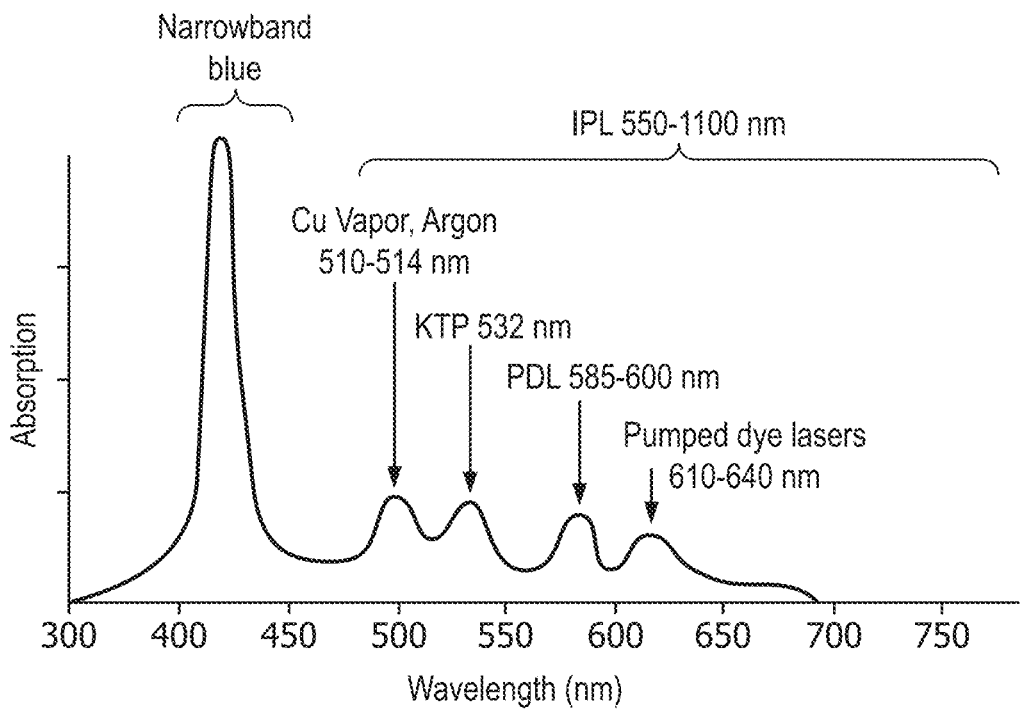
FIG. 1 shows an absorption profile of different wavelengths of light.
Figure 2:
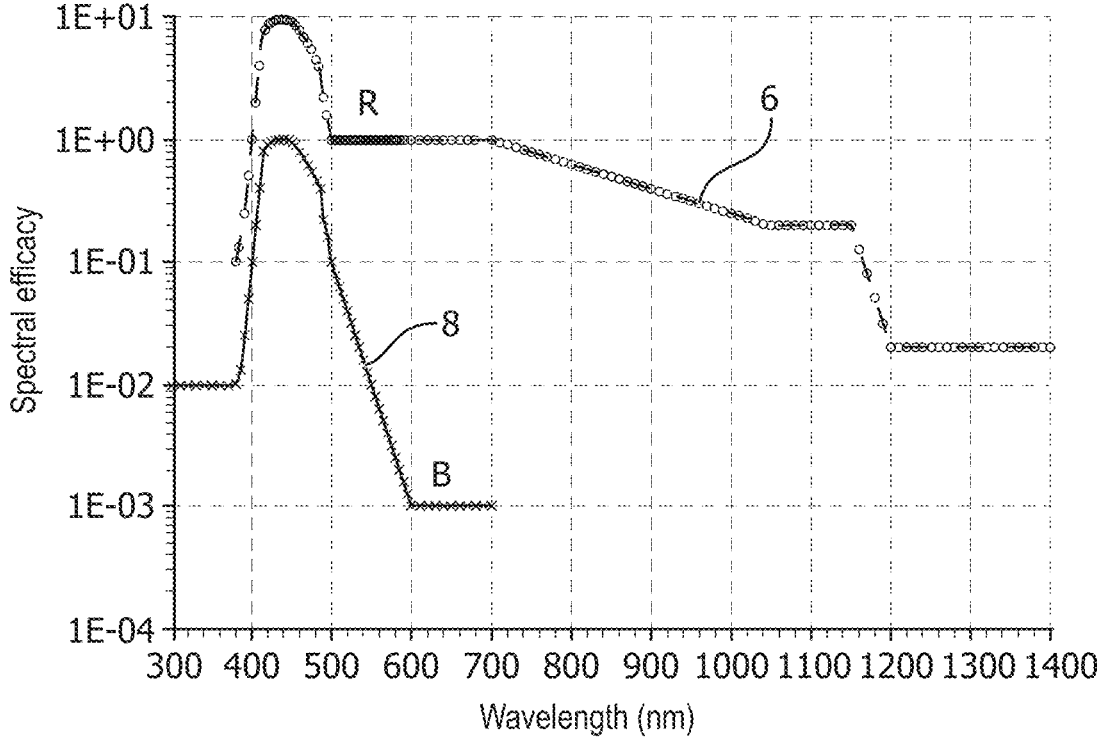
FIG. 2 shows spectral weighting functions for retinal hazards for two different colors of light.

The invention will be described with reference to the Figures.

It should be understood that the detailed description and specific examples, while indicating exemplary embodiments of the present invention, are intended for purposes of illustration only and are not intended to limit the scope of the invention. These and other features, aspects, and advantages of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a hair-cutting head for a hair-cutting device having two sets of light sources which are configured to emit light predominantly in different respective wavelength bands. A first set emits light predominantly in a wavelength band of 400-500 nm. A second set emits light predominantly in a wavelength band of 500 nm and above. For improved eye safety, the first set of light sources is arranged so that its light output is projected onto the user's skin during operation only via a central region of a skin-contacting area of the hair-cutting head. The second set of light sources is arranged to that its light output is provided on the user's skin during operation only via a peripheral region of the skin-contacting area of the hair-cutting head. This arrangement aims to make it more likely that the light of the first set of light sources is fully shielded by the contact of skin to the hair-cutting head during normal operation, protecting the eyes from this light.

One set of embodiments relates to a hair-cutting head for a shaver device, so that the hair-cutting head is a shaver head. However, this is only one example of a type of hair-cutting head to which the inventive concept could be usefully applied. It is to be understood that, in descriptions below that describe features in the context of a shaver device, the same features may be applied also to any other type of hair-cutting device and hair-cutting head.

One particular set of embodiments relates to a shaving system with embedded blue and red LEDs, wherein the spatial arrangement of the LEDs is configured to provide optimal user eye safety in particular for the blue light. In particular, the blue light sources are centrally embedded into the shaving head, while the red light sources are laterally embedded. The system may optionally also feature skin contact and/or motion sensors, where at least the blue light and preferably also the red light are controlled by a controller, such as an artificial intelligence. AI, system, which receives input from these sensors. Again, this describes one advantageous embodiment of the inventive concept, and is not restrictive of the broader scope of the inventive concept.

One aspect of the invention provides the hair-cutting head alone. Another aspect of the invention provides a hair-cutting device which comprises the hair-cutting head as a physically separable or physically integral part.

One example hair-cutting device and hair-cutting head, which embody the inventive concept, will now be described in detail by way of illustration.

Figures 3, 4:
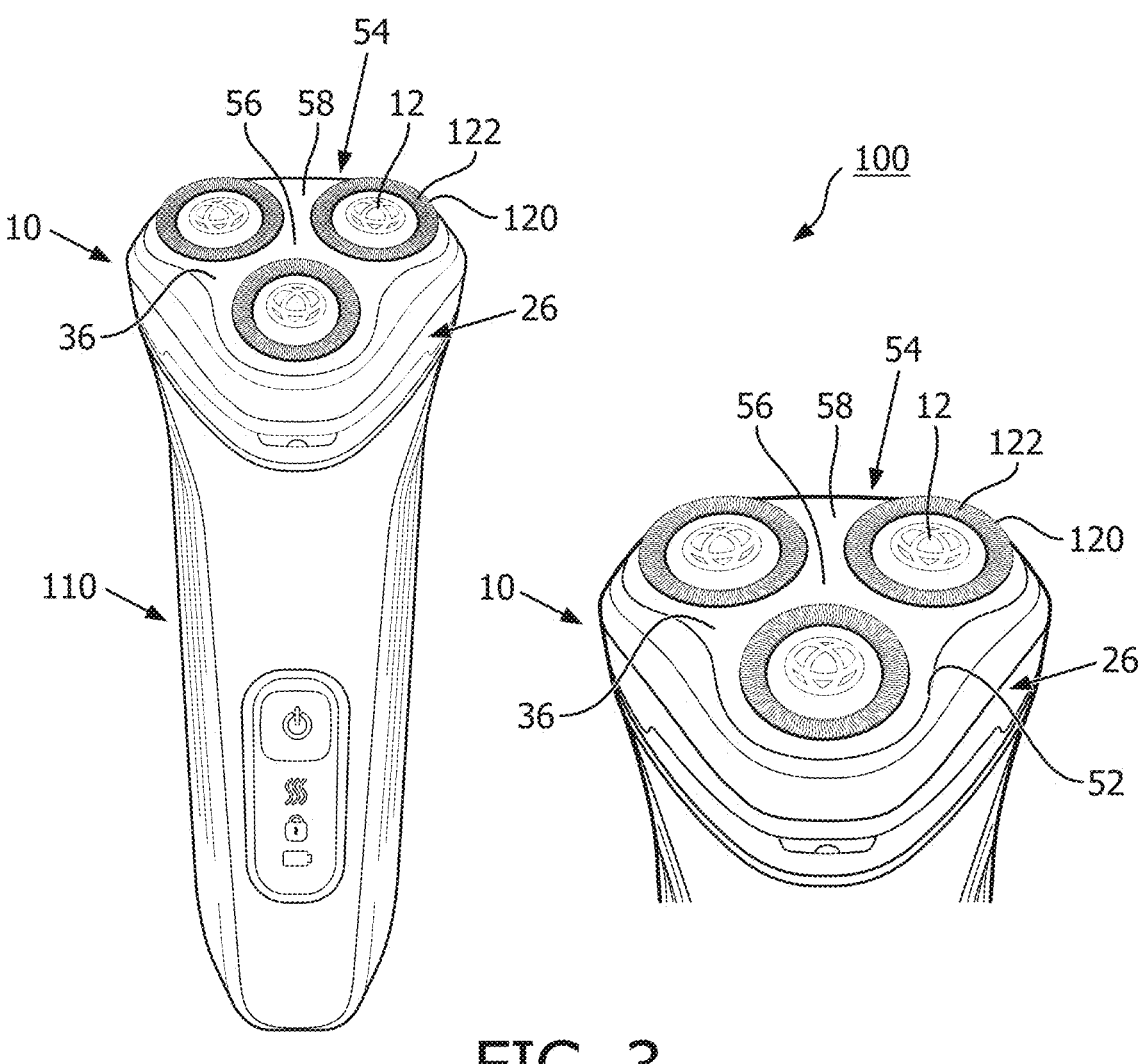
FIG. 3 illustrates an example hair-cutting device and an example hair-cutting head in accordance with at least one embodiment of the invention.
FIG. 4 schematically illustrates a cross-section through a hair-cutting head according to one or more embodiments of the invention.

FIG. 3 shows a first perspective view of the visible exterior of an example hair-cutting head 10 for a hair-cutting device 100. In this particular example, the hair-cutting head is a shaving unit 10, and the hair-cutting device is an electric shaver 100. In the shown example, the hair-cutting device 100 is a rotary type electric shaver (although this is not essential) and comprises a main body 110 that is intended to be taken hold of by a user of the hair-cutting device 100, and a hair-cutting head 10 that is intended to contact a portion of skin to be subjected to a hair-cutting action.

The main body 110 of the hair-cutting device 100 is also commonly referred to as a handle portion. For various reasons, such as a need to service and/or clean the hair-cutting head 10, a need to replace the hair-cutting head 10 by a functional unit of another type, etc., it is practical if the hair-cutting head 10 is removably or hingably mounted to the main body 110. The hair-cutting head 10 comprises a head housing 26 which accommodates a number of hair-cutting units 12, the number being three in the shown example. In the shown example, the hair-cutting units 12 are arranged in a generally triangular formation. When the hair-cutting device 100 is applied for the purpose of subjecting a portion of skin to a hair-cutting action, the actual process of cutting off hairs protruding from the portion of skin takes place at the position of the hair-cutting units 12.

Each of the hair-cutting units 12 comprises a combination of an external cutting member 120 that is of a generally cup-shaped design and an internal cutting member (not shown) that is equipped with at least one hair-cutting element and that is at least partially accommodated in the interior of the external cutting member 120. The external cutting member 120 has hair-entry openings 122 in an annular cutting track surface. During a hair-cutting action, hairs extending through the hair-entry openings 122 and protruding to the interior of the external cutting member 120 are cut off as soon as they are encountered by a hair-cutting element of the internal cutting member. A hair-cutting action as mentioned can be performed when the internal cutting member is activated to rotate and a portion of skin is actually contacted by the external cutting member 120 at the position of the cutting track surface. Activation of the internal cutting member may take place in a known manner by means of a drive mechanism (not shown) of the hair-cutting device 100 comprising an electric motor (not shown) arranged in the main body 110. The main body 110 may house the drive mechanism, optionally along with a local power source (e.g. battery). When the combination of the external cutting member 120 and the internal cutting member is moved over the portion of skin while the internal cutting member is driven to rotate, it is achieved that hairs protruding from the portion of skin are caught in the hair-entry openings 122 of the external cutting member 120 and are cut off in that position by the rotating internal cutting member.

It is noted that the invention also covers hair-cutting devices and hair-cutting heads having one or more hair-cutting units 12 of a different type as described herein before. In particular the invention also covers hair-cutting devices and hair-cutting heads having hair-cutting units with an internal cutting member arranged to linearly reciprocate relative to an external cutting member. These type of hair cutting devices include foil-type external cutting members for example.

The hair-cutting head 10 upper surface comprises a skin-contacting area 54, which encompasses a skin-contacting surface 36 of the hair-cutting head 10, and further encompasses the skin-contacting faces of the hair-cutting units 12. The skin-contacting area 54 is designed to be in contact with a user's skin during use of the hair-cutting head 10. The skin-contacting surface 36 is arranged to be in contact with the user's skin during use of the hair-cutting head. The skin-contacting surface 36 comprises, for each respective hair-cutting unit 12, an individual opening receiving the respective hair-cutting unit 12. Another way of describing this is that the skin-contacting area 54 comprises a skin-contacting surface 36 which delimits openings into which are accommodated each of the hair-cutting units 12. The skin contacting surface 36 surrounds each the hair-cutting units 12.

With reference to the schematic drawing of FIG. 4 in combination with FIG. 3, the skin contacting area 54 comprises a central area 56 and a lateral area 58 which fully surrounds the central area 56. The lateral area 58 of the skin-contacting area 54 is bounded by a perimeter of the skin-contacting area 54. More particularly, it is bounded by a perimeter 52 of the hair-cutting head 10.

With reference to FIG. 4, the head housing 26 of the hair-cutting head 10 further accommodates a lighting module 14. The lighting module 14 comprises a plurality of light sources 22, 24. The light sources may comprise one or more LEDs. The light sources of the lighting module 14 may be contained in a lighting module housing, or may simply comprise a collection of light sources distributed within the head housing 26 (as shown in FIG. 4). For simplicity. FIG. 4 does not show the hair-cutting units 12, but schematically shows only the central and lateral positions of the light sources relative to the head housing 26.

It is noted that although in FIG. 4 (and in other schematic drawings), the light sources 22, 24 are shown as having light output surfaces approximately co-planar with the skin contacting area 54, in practice the light sources may be arranged such that their light output surfaces are spaced vertically from the skin contacting area 54. This helps to avoid concentrated light hot-spots on the skin, and helps instead to provide a more uniform or even spread of light on the skin. For example, the light sources may be mounted within the head housing 26 at a defined vertical spacing from the skin contacting area 54. Additionally, a diffuser element (not shown) may be positioned between the light sources 22, 24 and the skin contacting area, to help provide a more uniform illumination.

As shown, the lighting module 14 comprises a first set of one or more light sources 22, and a second set of one or more light sources 24. Each set comprises at minimum at least one respective light source.

Each light source 22 of the first set of light sources is configured to emit first light having wavelengths predominantly in a range from 400-500 nm.

Each light source 24a. 24b of the second set of light sources is configured to emit second light having wavelengths predominantly in a range above 500 nm.

Although the first set of light sources 22 is shown comprising only one light source 22, it may instead comprise more than one light source. Although the second set of light sources 24a. 24b is shown comprising two light sources 24a. 24b it may instead comprise more than or fewer than two light sources.

Each light source 22 of the first set is arranged to emit, during use of the hair-cutting head 10 with the skin-contacting area 54 in contact with the user's skin, the first light towards the user's skin only via the central area 56 of the skin-contacting area 54. Each light source 24a. 24b of the second set is arranged to emit, during use of the hair-cutting head 10 with the skin-contacting area 54 in contact with the user's skin, the second light towards the user's skin only via the lateral area 58 of the skin-contacting area.

Figure 5:
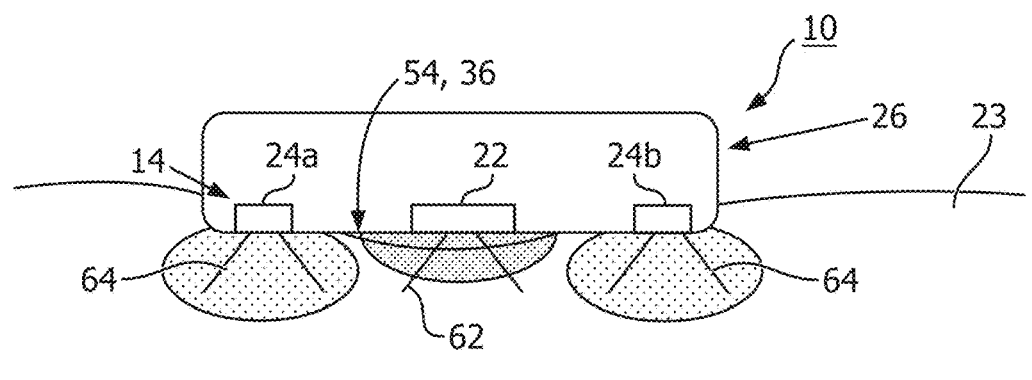
FIG. 5 schematically illustrates an example hair-cutting head in use according to one or more embodiments of the invention.

This is illustrated further, in schematic form, in FIG. 5 which shows the hair-cutting head 10 in contact with skin 23 of the user. Again, for simplicity the hair-cutting units 12 are not shown. As previously mentioned, the skin-contacting area 54 comprises a skin-contacting surface 36 of the head housing 26 which surrounds the exposed operative faces of the hair-cutting units 12. The light sources 22, 24 are positioned so as to provide their respective light outputs into the skin via respective portions of the skin-contacting area 54.

In particular, the central area 56 of the skin-contacting area 54 previously referred to comprises a central portion of the skin-contacting surface 36 of the head housing 26 arranged centrally between the hair-cutting units 12. The lateral area 58 of the skin-contacting area 54 comprises a lateral portion of the skin-contacting surface 36 of the head housing 20 that fully surrounds the central portion of the skin-contacting surface 36 and at least partially surrounds each of the hair-cutting units 12. Each light source 22 of the first set is arranged to emit, during use of the hair-cutting head 10, the first light 62 towards the user's skin 23 only via the central portion of the skin-contacting surface 36 of the head housing 26. Each light source 24a. 24b of the second set is arranged to emit, during use of the hair-cutting head, the second light 64 towards the user's skin 23 only via the lateral portion of the skin-contacting surface 36 of the head housing 26. The first light 62, by virtue of being emitted into the skin 23 at a more central location on the skin-contacting surface 36, is better shielded by the skin against escape into the region above the skin, and potentially into an eye of the user.

Figure 6:
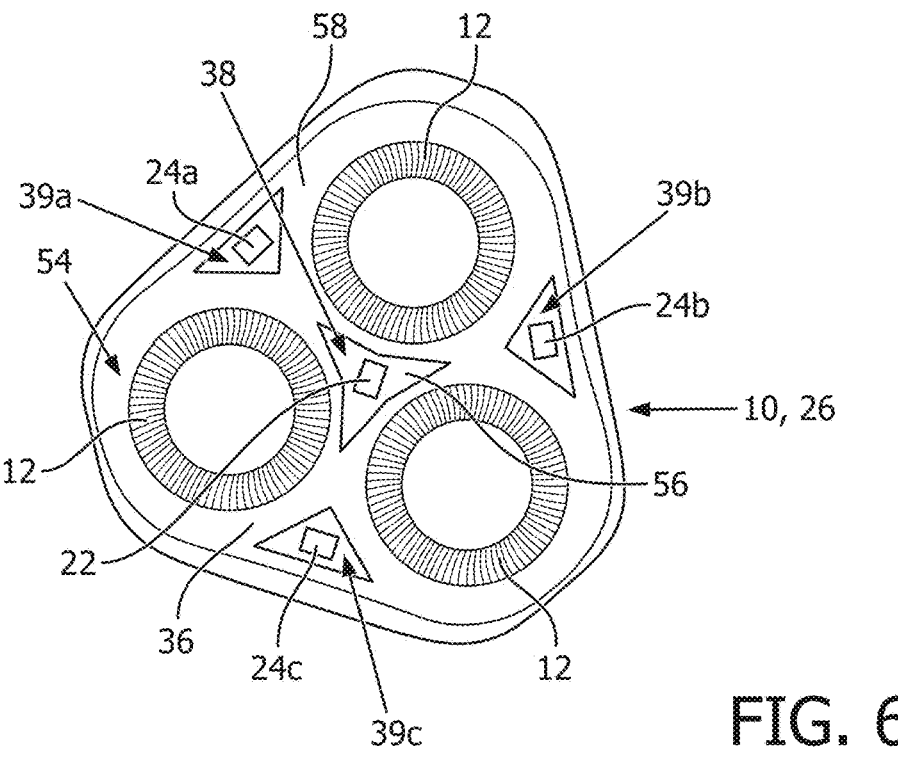
FIG. 6 illustrates the layout of light sources in an example hair-cutting head according to one or more embodiments of the invention.

The structure described above with reference to FIG. 4 and FIG. 5 is shown more clearly in FIG. 6. This illustrates the hair-cutting head 10, in particular for an electric hair-cutting device comprising three hair-cutting units 12 of a rotary type arranged in a tri-angular configuration forming three pairs of adjacent hair-cutting units 12.

As previously discussed with reference to FIG. 1, each hair-cutting unit 12 comprises an external cutting member with an annular hair-cutting area having hair-entry openings, and an internal cutting member which is covered by and rotatable relative to the external cutting member.

The central area 56 of the skin-contacting area 54 and the lateral area 58 of the skin contacting area 54 are indicated in FIG. 6. The lateral area 58 fully surrounds the central area 56. The lateral area constitutes a substantially triangularly shaped area.

The skin contacting surface 36 is the surface surrounding and extending in-between the three hair-cutting units 12.

The central area 56 of the skin-contacting area 54 previously referred to encompasses a central portion 38 of the skin-contacting surface 36 arranged centrally between the hair-cutting units 12. The lateral area 58 of the skin-contacting area previously referred to encompasses a lateral portion 39 of the skin-contacting surface that fully surrounds the central portion 38 of the skin-contacting surface 36 and at least partially surrounds each of the hair-cutting units 12.

The central portion 38 of the skin-contacting surface 36 of the head housing 26 is arranged centrally between the three hair-cutting units 12. The light source 22 of the first set is arranged to emit, during use of the hair-cutting head 10, the first light towards the user's skin only via the central portion 38 of the skin-contacting surface 36.

The lateral portion 39 of the skin-contacting surface 36 of the head housing 26 comprises three lateral sub-portions 39a. 39b. 39c that are each respectively arranged between the hair-cutting units 12 of a respective pair of the three pairs of adjacent hair-cutting units 12, as shown in FIG. 6.

The second set of light sources 24 comprises, for each respective one of the three lateral sub-portions 39a. 39b. 39c of the lateral portion 39 of the skin-contacting surface 36, at least one light source 24a. 24b. 24c arranged to emit the second light towards the user's skin only via said respective lateral sub-portion 39a. 39b. 39c.

It is noted that the above-described hair-cutting head 10 comprising three rotary-type hair-cutting units 12 is presented as merely one enabling example of a device which may embody the inventive concept. More generally, the inventive concept is not limited to any particular structure or arrangement of the hair-cutting units within the hair-cutting head. For example, rotary-type shavers comprising more than three hair-cutting units or fewer than three hair-cutting units are also encompassed. Furthermore, shaver devices of a foil-type, rather than rotary type, are also encompassed. For example, in accordance with one further set of embodiments, the hair-cutting head may comprise two hair-cutting units, each with a foil-type external cutting member extending in a longitudinal direction and having hair-entry openings, and an internal cutting member arranged to linearly reciprocate relative to the external cutting member in the longitudinal direction. In such shavers for example the first set of light sources 22 may be arranged in the (longitudinal) central area between the two hair-cutting units along a first longitudinal side of each of the two hair-cutting units facing the central area, and the second set of light sources 24 may be arranged along a second longitudinal side of each of the two hair-cutting units opposite to the first longitudinal side.

According to one advantageous set of embodiments, the first set of light sources 22 may be adapted to emit blue light, and the second set of light sources 24 may be adapted to emit red light. In this regard, the first light 62 of the first set of light sources 22 may have wavelengths predominantly in a range from 400-480 nm.

The second light 64 of the second set of light sources 24 may have wavelengths predominantly in a range from 600-700 nm.

Thus, according to this set of embodiments, the blue light sources are centrally embedded into the hair-cutting head 10, while the red light sources are laterally embedded into the hair-cutting head 10. The blue light is absorbed into the first layers of the skin and it does not scatter deeply into the skin layers. Therefore, placing the blue LEDs centrally improves eye safety.

In addition to spatially differentiating the light output of the first set of light sources 22 and the light output of the second set of light sources 24, the light output of at least the first set of light sources 22 can also be temporally regulated according to at least one set of embodiments.

Figure 7:
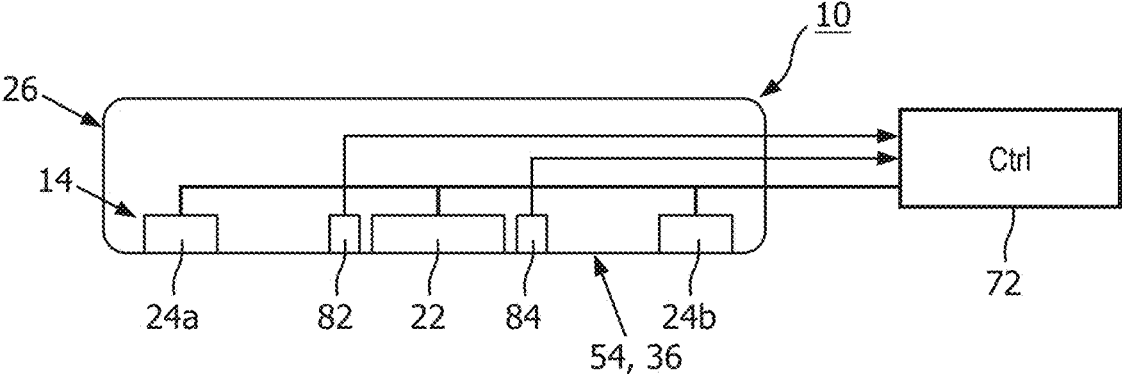
FIG. 7 schematically illustrates an electrical control configuration of an example hair-cutting unit according to one or more embodiments of the invention.

In particular, and with reference to FIG. 7, the hair-cutting head 10 may comprise a skin contact sensor 82 and/or a motion sensor 84 in order to detect whether the skin-contacting area 54 of the hair-cutting head 10 is in contact with the user's skin and/or to detect motion of the hair-cutting head 10 relative to the user's skin. The skin-contact sensor 82 and the motion sensor 84 may be located in the hair-cutting head 10 in positions close to the position of the first set of light sources 22, as schematically shown in FIG. 7.

With reference to FIG. 7, in some embodiments the hair-cutting head 10 comprises a skin contact sensor 82 configured and arranged to detect, during use of the hair-cutting head, contact between at least a region of the skin-contacting area 54 of the hair-cutting head 10 and the user's skin. The skin contact sensor 82 may have a sensing part mechanically or capacitively coupled with the skin contacting surface 36 of the head housing 26. In other examples, the skin contact sensor 82 could be integrated with at least one of the hair-cutting units 12 such that application of the hair-cutting unit 12 to the skin causes the skin contact sensor 82 to indicate skin contact.

A controller 72 is further provided which is operatively coupled with the skin contact sensor 82. The controller may be integrated as part of the hair-cutting head 10, e.g. integrated in the head housing 26, or it may be integrated in the main body 110 of the hair-cutting device 100 (see FIG. 3). The controller 72 is adapted to control the lighting module 14 such that at least each light source 22 of the first set of light sources is prevented from emitting the first light when an output signal generated by the skin contact sensor 82 indicates no contact with the user's skin. The controller 72 may also control the light sources 24a. 24b of the second set of light sources to be prevented from emitting the second light when the skin contact sensor 82 indicates no contact with the user's skin. As shown, the skin contact sensor 82 is in this example arranged in the central area of the skin-contacting area 54, although this is not essential.

Optionally, in addition to or instead of the skin contact sensor 82, a motion sensor 84 may be provided in the hair-cutting head 10. The motion sensor 84 is configured and arranged to detect, during use of the hair-cutting head 10, motion of the hair-cutting head 10 relative to the user's skin. The controller 72 may be adapted to control the lighting module 14 such that at least each light source 22 of the first set of light sources is prevented from emitting the first light when an output signal generated by the motion sensor 84 indicates, relative to the user's skin, no motion of the hair-cutting head 10 or motion of the hair-cutting head 10 at a speed below a predefined threshold speed. Optionally, the light sources 24a. 24b of the second set of light sources may also be prevented by the processor 72 from emitting the second light when the motion sensor 84 detects no motion or motion at a speed below the threshold speed.

In some embodiments, both a skin contact sensor 82 and a motion sensor 84 may be provided. In such embodiments, at least the first set of light sources is controlled to be inactive when no skin contact is detected or when there is no motion relative to the skin or motion below the pre-defined threshold speed. The use of the motion sensor 84 avoids over exposure of a certain area of the skin to at least the first light of the light sources 22 of the first set.

With regards to the controller, this can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

In some embodiments, the controller may comprise an artificial intelligence algorithm for performing the above-discussed control functions. This may comprise a machine learning algorithm such as a Convolutional Neural Network (CNN) for example.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A hair-cutting head for a hair-cutting device, comprising:
   a head housing accommodating at least one hair-cutting unit and a lighting module;
   a skin-contacting area via which the hair-cutting head is in contact with a user's skin during use of the hair-cutting head and having a central area and a lateral area that fully surrounds the central area;
wherein:
   the lighting module comprises a first set of at least one light source each configured to emit first light having wavelengths predominantly in a range from 400-500 nm, and a second set of at least one light source configured to emit second light having wavelengths predominantly in a range above 500 nm;
   each light source of the first set is arranged to emit, during use of the hair-cutting head with the skin-contacting area in contact with the user's skin, the first light towards the user's skin only via the central area of the skin-contacting area;
   each light source of the second set is arranged to emit, during use of the hair-cutting head with the skin-contacting area in contact with the user's skin, the second light towards the user's skin only via the lateral area of the skin-contacting area.

2. A hair-cutting head as claimed in claim 1, wherein the lateral area of the skin-contacting area is bounded by a perimeter of the skin-contacting area.

3. A hair-cutting head as claimed in claim 1, comprising at least two hair-cutting units, wherein:
   the head housing comprises a skin-contacting surface arranged to be in contact with the user's skin during use of the hair-cutting head;
   the skin-contacting surface comprises, for each respective hair-cutting unit, an individual opening receiving the respective hair-cutting unit;
   the central area of the skin-contacting area comprises a central portion of the skin-contacting surface arranged centrally between the hair-cutting units;
   the lateral area of the skin-contacting area comprises a lateral portion of the skin-contacting surface that fully surrounds the central portion of the skin-contacting surface and at least partially surrounds each of the hair-cutting units;
   each light source of the first set is arranged to emit, during use of the hair-cutting head, the first light towards the user's skin only via the central portion of the skin-contacting surface of the head housing;
   each light source of the second set is arranged to emit, during use of the hair-cutting head, the second light towards the user's skin only via the lateral portion of the skin-contacting surface of the head housing.

4. A hair-cutting head as claimed in claim 3, in particular for an electric hair-cutting device comprising three hair-cutting units of a rotary type arranged in a tri-angular configuration forming three pairs of adjacent hair-cutting units, wherein:
   each hair-cutting unit comprises an external cutting member with an annular hair-cutting area having hair-entry openings, and an internal cutting member which is covered by and rotatable relative to the external cutting member;
   the central portion of the skin-contacting surface of the head housing is arranged centrally between the three hair-cutting units;

the lateral portion of the skin-contacting surface of the head housing comprises three lateral sub-portions that are each respectively arranged between the hair-cutting units of a respective pair of the three pairs of adjacent hair-cutting units;

the second set comprises, for each respective one of the three lateral sub-portions of the lateral portion of the skin-contacting surface, at least one light source arranged to emit the second light towards the user's skin only via said respective lateral sub-portion.

5. A hair-cutting head as claimed in claim 1, wherein the first light has wavelengths predominantly in a range from 400-480 nm.

6. A hair-cutting head as claimed in claim 1, wherein the second light has wavelengths predominantly in a range from 600-700 nm.

7. A hair-cutting head as claimed in claim 1, further comprising:

a skin contact sensor configured and arranged to detect, during use of the hair-cutting head, contact between at least a region of the skin-contacting area of the hair-cutting head and the user's skin;

a controller adapted to control the lighting module such that at least each light source of the first set is prevented from emitting the first light when an output signal generated by the skin contact sensor indicates no contact with the user's skin.

8. A hair-cutting head as claimed in claim 7, wherein the skin contact sensor is arranged in the central area of the skin-contacting area.

9. A hair-cutting head as claimed in claim 1, further comprising:

a motion sensor configured and arranged to detect, during use of the hair-cutting head, motion of the hair-cutting head relative to the user's skin;

a controller adapted to control the lighting module such that at least each light source of the first set is prevented from emitting the first light when an output signal generated by the motion sensor indicates, relative to the user's skin, no motion of the hair-cutting head or motion of the hair-cutting head at a speed below a predefined threshold speed.

10. A hair-cutting device comprising a handle portion and a hair-cutting head coupled to the handle portion, wherein the hair-cutting head is a hair-cutting head as claimed in claim 1.

11. A hair-cutting device as claimed in claim 10, wherein:

the hair-cutting device is an electric shaver;

the handle portion comprises a main housing of the electric shaver accommodating an electric motor;

the hair-cutting head is a shaving unit;

the motor is configured and arranged to drive each of the hair-cutting units of the shaving unit when the shaving unit is coupled to the main housing.

\* \* \* \* \*